US011987782B2

(12) United States Patent
Glaven et al.

(10) Patent No.: US 11,987,782 B2
(45) Date of Patent: May 21, 2024

(54) BIOFILM BIOREACTOR

(71) Applicant: The Government of the United States of America, as represented by the Secretary of the Navy, Arlington, VA (US)

(72) Inventors: Sarah Glaven, Washington, DC (US); Elizabeth Onderko, Alexandria, VA (US); Andrew Maygar, Arlington, VA (US); Matthew Yates, Centreville, MA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 584 days.

(21) Appl. No.: 17/178,488

(22) Filed: Feb. 18, 2021

(65) Prior Publication Data

US 2021/0253990 A1    Aug. 19, 2021

Related U.S. Application Data

(60) Provisional application No. 62/978,428, filed on Feb. 19, 2020.

(51) Int. Cl.
| | |
|---|---|
| *C12M 1/00* | (2006.01) |
| *C12M 1/04* | (2006.01) |
| *C12M 1/12* | (2006.01) |
| *C12M 1/34* | (2006.01) |
| *C12M 3/00* | (2006.01) |
| *C12P 7/04* | (2006.01) |

(52) U.S. Cl.
CPC ............ *C12M 23/44* (2013.01); *C12M 21/12* (2013.01); *C12M 23/24* (2013.01); *C12M 23/58* (2013.01); *C12M 25/10* (2013.01); *C12M 29/16* (2013.01); *C12M 41/28* (2013.01); *C12P 7/04* (2013.01)

(58) Field of Classification Search
None
See application file for complete search history.

(56) References Cited

U.S. PATENT DOCUMENTS

| 2012/0178123 | A1 | 7/2012 | Rosen | |
| 2013/0211143 | A1* | 8/2013 | Granstrom | ................ C12P 7/16 435/150 |
| 2014/0303408 | A1* | 10/2014 | Zaher | ..................... C07C 29/86 568/913 |

FOREIGN PATENT DOCUMENTS

| EP | 0605173 | A2 | 7/1994 | |
| JP | 06319520 | A * | 11/1994 | ............ C12M 21/02 |
| KR | 2019068145 | A * | 6/2019 | ............ C12M 25/16 |

(Continued)

OTHER PUBLICATIONS

Davison et al. "Continuous Direct Solvent Extraction of Butanol in a Fermenting Fluidized-Bed Bioreactor with Immobilized Clostridium acetobutylicum," Applied Biochemistry and Biotechnology, vol. 39/40, 1993, pp. 415-426. (Year: 1993).*

(Continued)

*Primary Examiner* — William H. Beisner
(74) *Attorney, Agent, or Firm* — US Naval Research Laboratory; Roy Roberts

(57) ABSTRACT

Described herein are biofilm bioreactors for synthesis at the interface between two liquids, and methods of using such bioreactors for the biotransformation of feedstocks into chemical products. Also contemplated is the extraction of such products.

15 Claims, 11 Drawing Sheets

Specification includes a Sequence Listing.

(56) References Cited

FOREIGN PATENT DOCUMENTS

| WO | WO-2009063138 A2 * | 5/2009 | ............... C10L 1/02 |
|---|---|---|---|
| WO | 2012152337 A1 | 11/2012 | |
| WO | 2019056071 A1 | 3/2019 | |

OTHER PUBLICATIONS

"A Previously Uncharacterized, Nonphotosynthetic Member of the Chromatiaceae Is the Primary CO2-Fixing Constituent in a Self-Regenerating Biocathode" Zheng Wang, Dagmar H. Leary, Anthony P. Malanoski, Robert W. Li, W. Judson Hervey IV, Brian J. Eddie, Gabrielle S. Tender, Shelley G. Yanosky, Gary J. Vora, Leonard M. Tender, Baochuan Lin, Sarah M. Strycharz-Glaven Applied and Environmental Microbiology. Jan. 2015, 81 (2) 699-712; DOI: 10.1128/AEM.02947-14.
Mishra et al. Chemosphere vol. 340 (2023) 39878.
Halan et al., Appl Environ Microbiol . . . 77 (2011) 1563-1571.
Epstein et al., Proceedings of the National Academy of Sciences, 108 (2011) 995-1000.

\* cited by examiner

BIOFILM BIOREACTOR

CROSS-REFERENCE TO RELATED APPLICATIONS

This application claims the benefit of U.S. Provisional Application 62/978,428 filed on Feb. 19, 2020, the entirety of which is incorporated herein by reference.

FEDERALLY-SPONSORED RESEARCH AND DEVELOPMENT

The United States Government has certain ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 112,479.

BACKGROUND

Fermentation and algae bioreactors are used to produce bioethanol, biodiesel and other products. In industrial scale biomanufacturing, typically a product is produced in a suspended cell reactor during so-called log-scale growth where biomass is undergoing periodic doublings. To extract the final product, downstream processing such as distillation or dehydration followed by solvent phase extraction can be required.

Biofilm bioreactors are a type of bioreactor that uses cells that are immobilized on a solid scaffold for the synthesis of a product. A variety of biofilm bioreactors have been developed for different applications, particularly for wastewater treatment. These include packed bed reactors (Holliday et al., 1978), which use a granular matrix packed within a column as a scaffold; two-phase partitioning bioreactors (Daugulis et al., 1997), wherein a non-aqueous phase is added to a microorganism-containing aqueous phase to facilitate the continual and gradual transfer of hydrophobic substrates into the aqueous phase; and extractive membrane bioreactors (Livingston, 1998), where a membrane separates an aerated biomedium and a feedstock (typically wastewater). Volatile organic compounds diffuse across the membrane and are degraded by a biofilm growing on the biomedium side of the reactor.

Biofilm bioreactors have utilized naturally-forming consortia of organisms and been applied for applications such as the removal of toxic materials from wastewater, or the production of products from gaseous sources such as carbon monoxide.

Hydrocarbonoclastic organisms such as *Marinobacter* spp. form biofilms and are able to uptake alkanes and aromatics (Gauthier et al., 1992; Lattuati et al., 2002; Ennouri et al., 2017; Mournier et al., 2018, Arroyo et al., 2013) and convert them into products such as wax esters, which have commercial value as lubricants. Organisms capable of accumulating lipids such as wax esters are commonly referred to as oleaginous. Evidence of extracellular neutral lipids produced by *Marinobacter* spp. have been reported by Nakano et al., 2012. These pathways can also be diverted to produce other products such as phloroglucinol (Meyer et al., 2019).

Additionally, organic solvents have been utilized as a means to periodically extract products from planktonically grown algae such as *B. brunaii* or *D. salina* in a process termed milking (Hejazi et al, 2004; Jackson et al., 2018; Hejazi et al., 2005; Sayre, 2009). The milking approach enables the non-destructive removal of hydrocarbons from a bioreactor into a solvent phase, which can dramatically reduce required downstream processing. Several systems have been developed for product extraction from milking. One, a mixer-settler system, operates in a continuous single stage. In a mixing segment, solvent and the culture medium are stirred to provide contact between the solvent and cells. The solvent culture mixture then transfers into a settling segment where a top solvent phase containing the product, and a bottom aqueous phase containing the cell fraction are separated. A second system, the column extractor, passes droplets of organic solution through a media solution to extract product. In both cases, the cells are planktonic, cultured in a separate vessel, and periodically transferred into the extraction system for removal.

The key challenges of biofilm-based processing include mass transfer limitations, control over biofilm formation, and challenges with product extraction.

BRIEF SUMMARY

In a first embodiment, a bioreactor includes a vessel comprising a solid support suitable for the growth of a biofilm; containment for a feedstock solution in contact with the biofilm; and a container for extraction solution configured to be delivered to the vessel containing the biofilm. The bioreactor is configured to host a biofilm-forming microorganism that is tolerant of both solutions and can carry out biotransformations. The feedstock provides a chemical source that can be biologically transformed into a desired product. The extraction solution, when in contact with the biofilm, enables the removal of the desired product. The biofilm-forming microorganism should be tolerant of both solutions and can carry out biotransformation of feedstock into the product. The microorganism preferably enjoys stable growth in the biofilm. The product can be extracted in a continuous or periodic (or batched) manner through exposure to the extraction solution.

For example, a bioreactor system might include a column comprising a substrate coated with a biofilm comprising hydrocarbonoclastic and/or oleaginous organisms; a first reservoir operably connected to deliver to the column a first liquid comprising a feedstock; a second reservoir operably connected to deliver a second liquid to the column; and a phase separator operably connected to receive both liquids from the column, wherein the biofilm is effective to convert the feedstock into a desired product, and wherein the phase separator is effective to separate the product from one or both of the liquids.

In a further embodiment, the bioreactor resembles a packed bed reactor, where a biofilm of a hydrocarbonoclastic and/or oleaginous organism is grown on beads packed in a column. During operation, the aqueous feedstock flows through the column to provide both nourishment for the biofilm and chemical compounds that are transformed by the organism into the desired product. Periodically, a bolus of an organic solvent is introduced into the reactor to harvest the product.

In another embodiment, the bioreactor resembles an extractive membrane bioreactor. In this embodiment, a porous scaffold is used to grow a high surface area biofilm of a hydrocarbonoclastic and/or oleaginous organism. The porosity may be designed so that the membrane growth fully closes the pores forming a barrier layer between the two solutions. Optionally, the membrane may be chemically selective for a particular product, with the biofilm growing solely on the feedstock side of the bioreactor.

In some embodiments, the membrane may be in a tubular geometry and contained in a column. Such a co-axial geometry would provide the ability to continually introduce a feedstock on one side of the biofilm and carry out extraction on the other side of the biofilm.

In yet other embodiments, a method of biotransformation includes providing a bioreactor of any of the previous embodiment (or combinations thereof), supplying it with feedstock and extraction solution, allowing a living biofilm-forming microorganism with the bioreactor to transform the feedstock into a product, and extracting the product.

For example, a method of converting a hydrophobic feedstock into aqueous phase product could include providing a bioreactor comprising a living microorganism capable of producing a water-soluble product; circulating nutritive media through the bioreactor to establish a biofilm of the microorganism; introducing both an aqueous solution and a hydrophobic feedstock into the bioreactor, wherein the aqueous solution provides supplemental nutrients to the microorganism; allowing the microorganism to convert the hydrophobic feedstock into the product; and recovering the product from the aqueous solution.

As another example, a method of converting an aqueous feedstock into hydrophobic product could include providing a bioreactor comprising a microorganism capable of producing a hydrophobic product; introducing a water-soluble feedstock into the bioreactor and allowing the microorganism to convert the feedstock into the hydrophobic product; contacting the microorganism with a solvent effective to extract the product; and then recovering the product from the solvent.

DETAILED DESCRIPTION

Definitions

Figure 1:
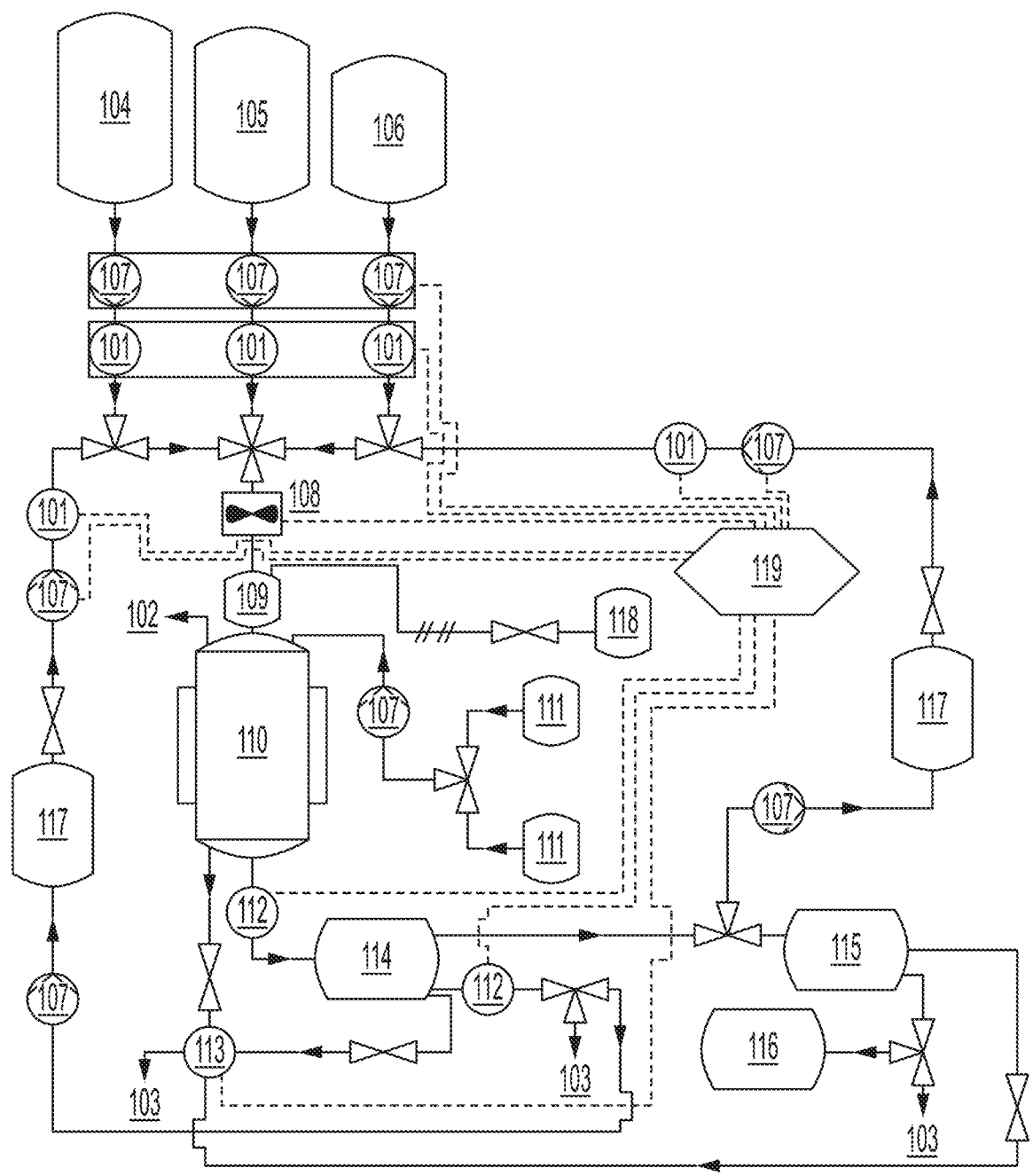
FIG. 1 shows an end-to-end schematic of an exemplary bioreactor system for conversion of a crude feedstock into a purified product. Depicted components include various flow controllers, each labeled 101, vent 102, waste 103, feedstock-containing vessel 104, supplemental nutrients 105, product extraction solvent (aqueous or non-aqueous) 106, pump 107, mixer 108, aerator 109, thermally-jacketed bioreactor 110, acid/base 111, sensors 112, output analysis 113, phase separator 114, product purification 115, product storage 116, recirculation reservoir tank 117, gas source 118, and computer 119.
Figure 2:
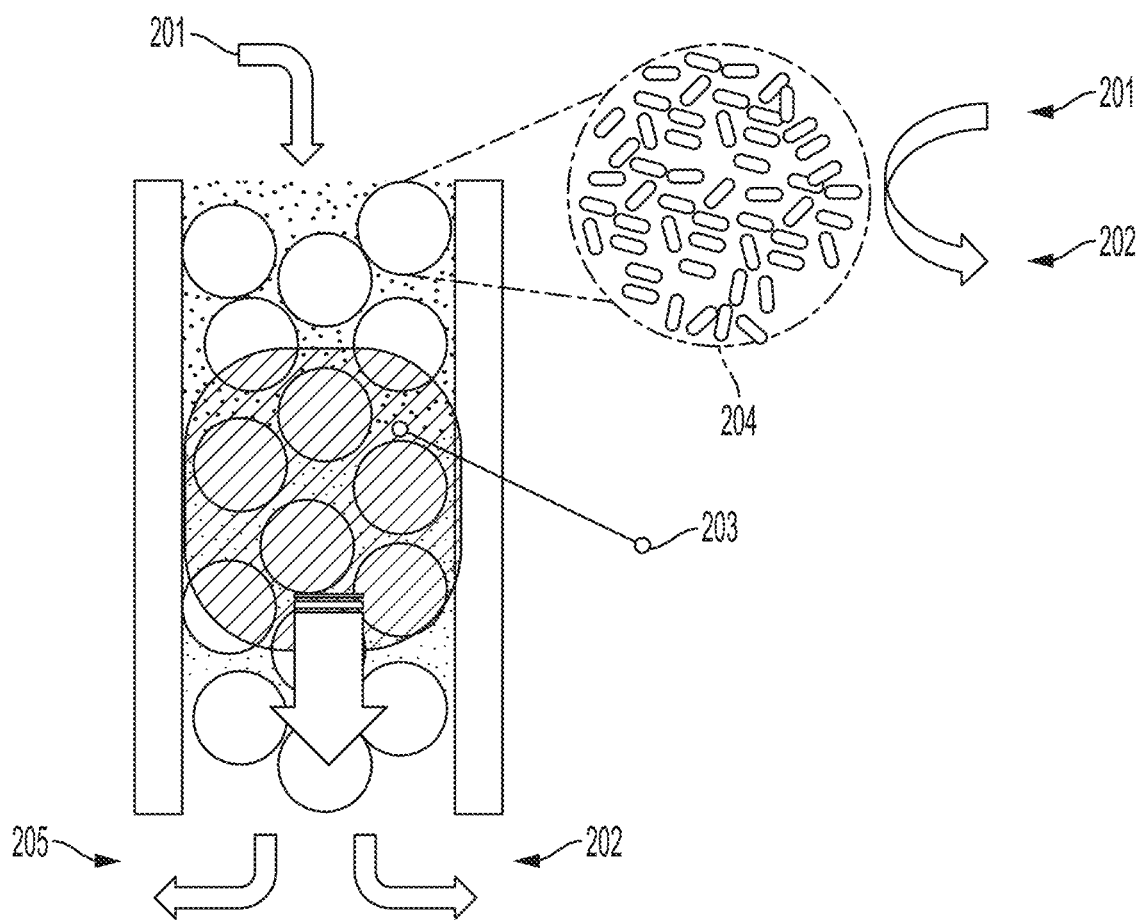
FIG. 2 depicts a cross-sectional view of an embodiment of the biofilm bioreactor with a packed-bed design wherein a solvent droplet is circulated through the reactor to extract product. In this figure, 201 represents feedstock (for example, fatty acids, oil, waste materials, and combinations thereof); 202 product (originally obtained in a solvent phase and which can comprise, for example, lubricants, fuels, fatty acids, vitamins, and the like); 203 organic solvent droplet operating to extract product; 204 carrier bead with biofilm (for example, incorporating *Marinobacter*); and 205 water (which can be recycled). An expanded view shows an individual carrier bead with the biofilm that carries out the biotransformation.
Figure 3:
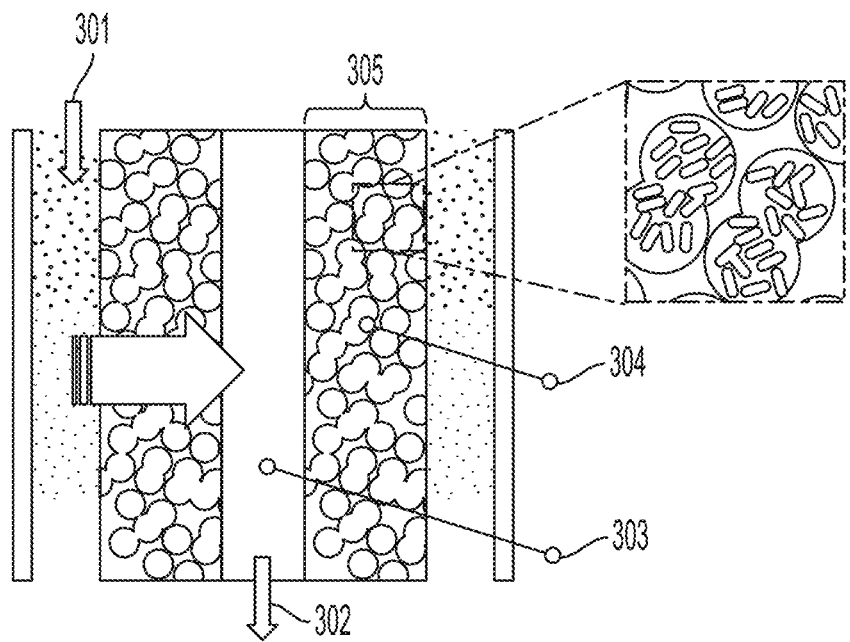
FIG. 3 depicts a cross-sectional view of an embodiment of the biofilm bioreactor where the biofilm is intercalated with or coats a membrane between the feedstock solution and the extraction solution. In this figure, 301 represents feedstock; 302 product (in a solvent phase); 303 organic solvent operating to extract product; and 304 microbial (e.g., *Marinobacter*) biofilm intercalated with the 305 membrane. An expanded view shows the biofilm within the membrane.
Figure 4:
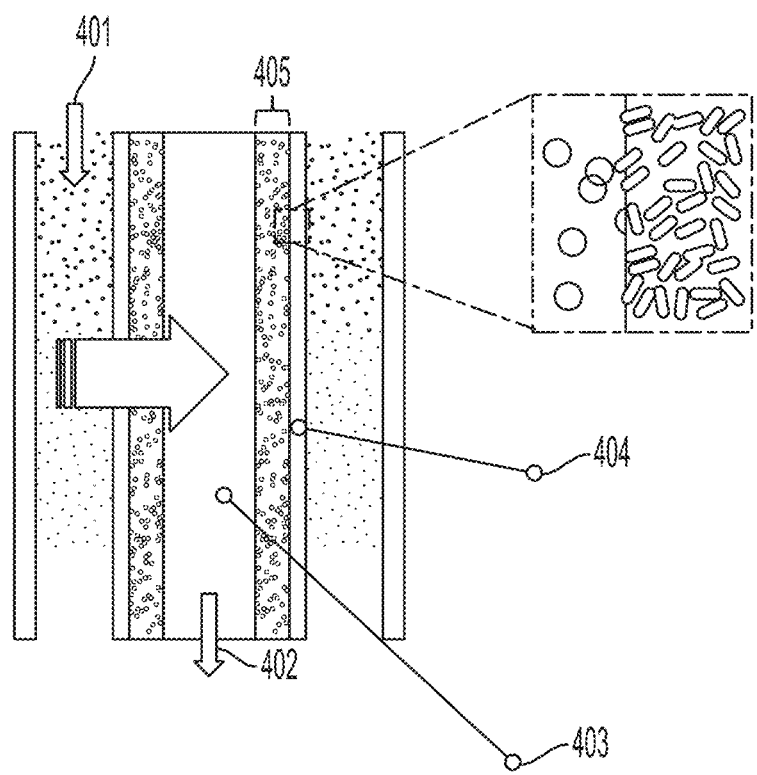
FIG. 4 depicts a cross-section view of an embodiment of the biofilm bioreactor where the biofilm is growing on one side of a membrane that, in some instances, may be chemically selective. In some embodiments, this membrane may have molecular selectivity. Here, 401 represents feedstock, 402 product (in a solvent phase), 403 organic solvent operating to extract product, and 404 microbial (e.g., *Marinobacter*) biofilm on the surface of a 405 membrane. The expanded view details the biofilm on the membrane.
Figure 5:
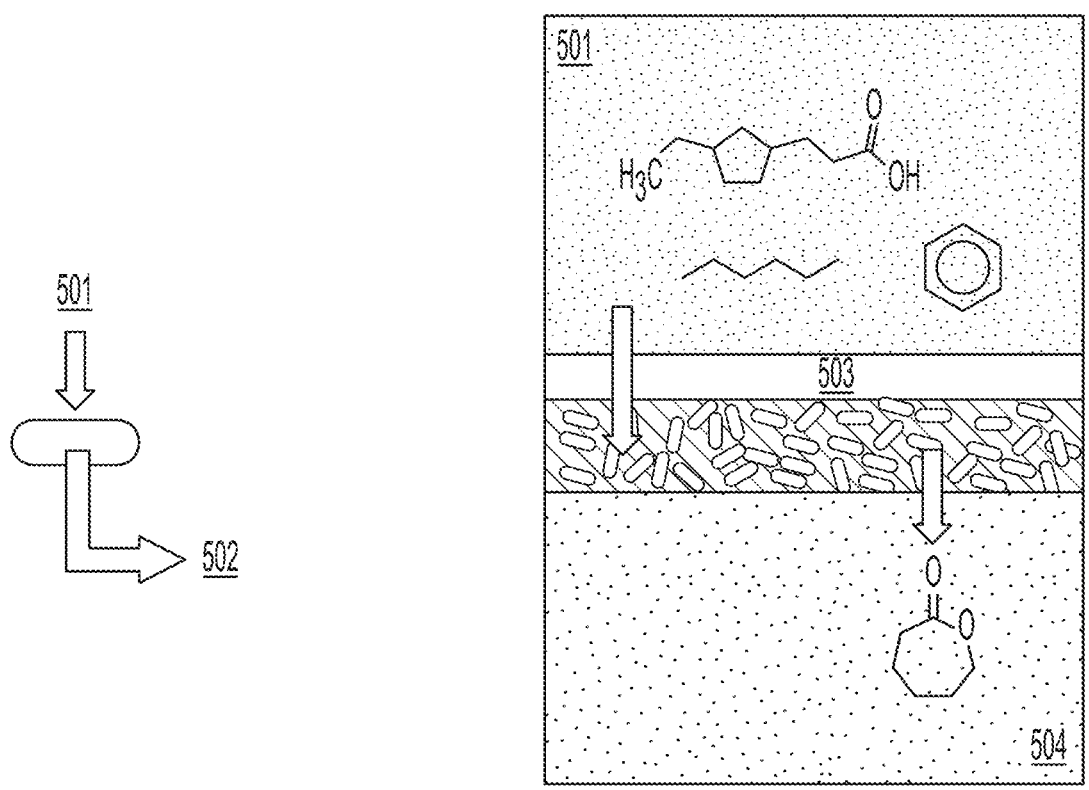
FIG. 5 depicts an example of transformation of a hydrophobic feedstock (e.g. petroleum) into a water-soluble product. In this figure, 501 represents hydrophobic feedstock (such as petroleum, alkanes, aromatics, and the like, to include combinations thereof); 502 water-soluble product, such as acetate, lactate, etc.; 503 membrane; and 504 aqueous phase collection.
Figure 6:
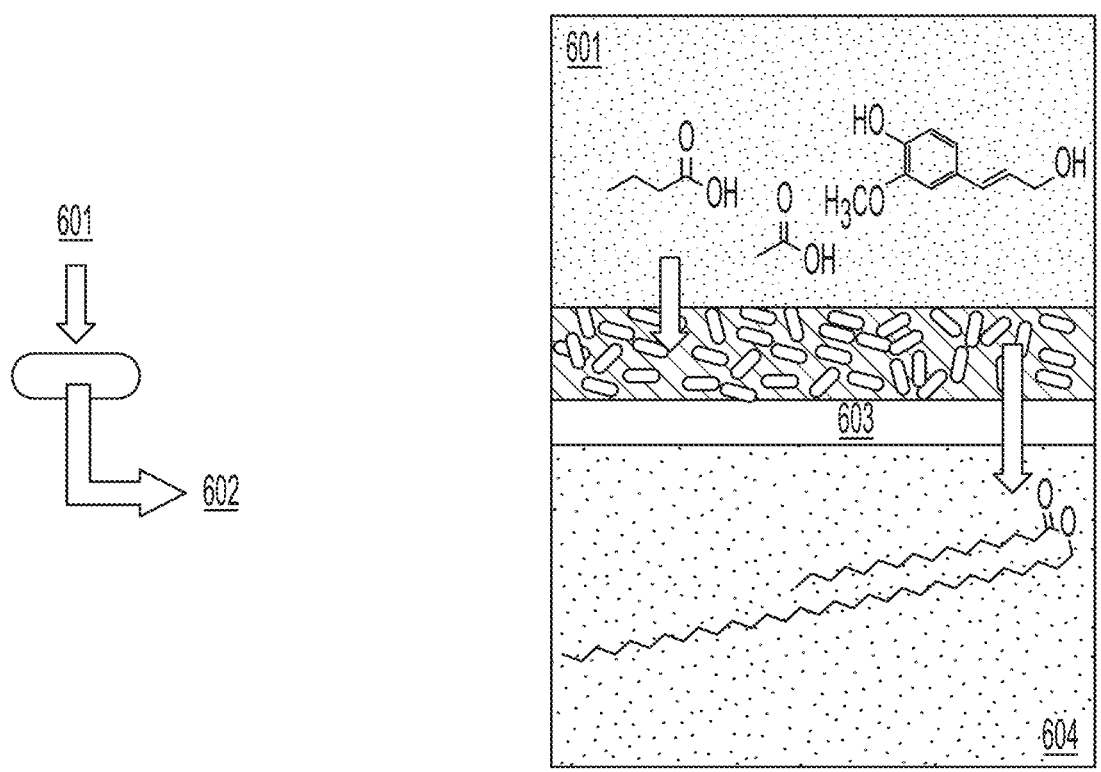
FIG. 6 depicts an example of biotransformation of aqueous mixed feedstock into a solvent-soluble (hydrophobic) product. Here, 601 represents aqueous feedstock (such as small chain fatty acids, sugars, liginols, and the like, to include combinations thereof); 602 hydrophobic product, such as wax esters, lubricants, styrene, etc.; 603 membrane; and 604 organic solvent for extraction.
Figure 7:
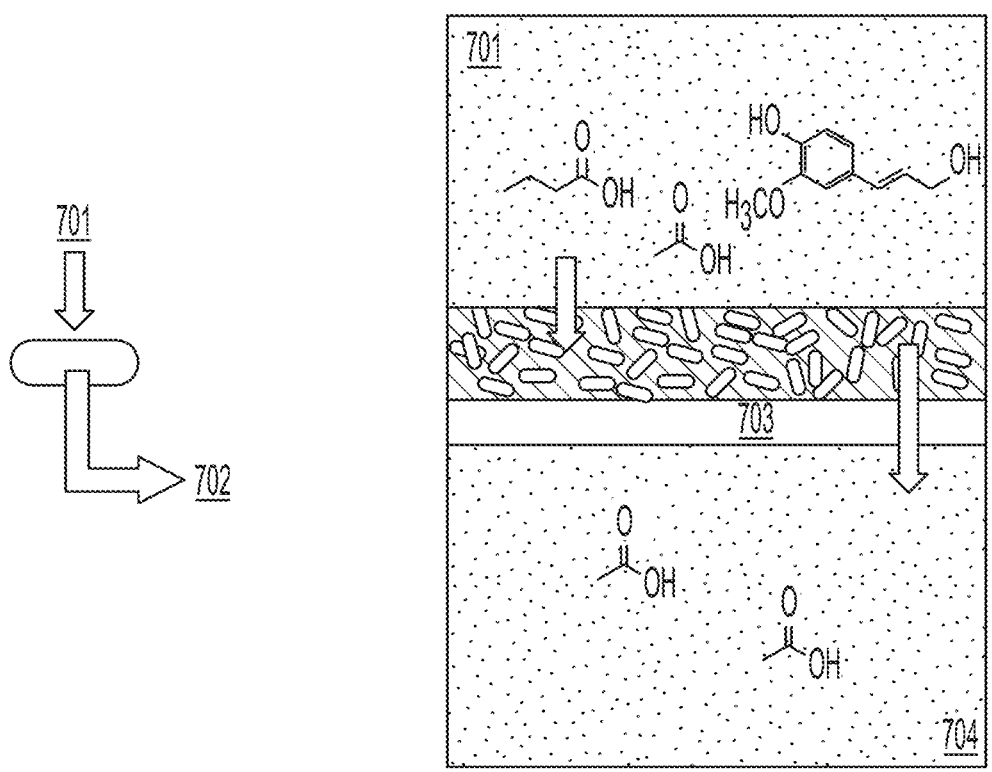
FIG. 7 depicts an example of biotransformation from aqueous to aqueous phase where the biofilm is grown on a selective membrane. In this figure, 701 represents aqueous feedstock (such as small chain fatty acids, sugars, liginols, and the like, to include combinations thereof); 702 water-soluble product, such as acetate, lactate, etc.; 703 membrane; and 704 aqueous extraction.
Figure 8:
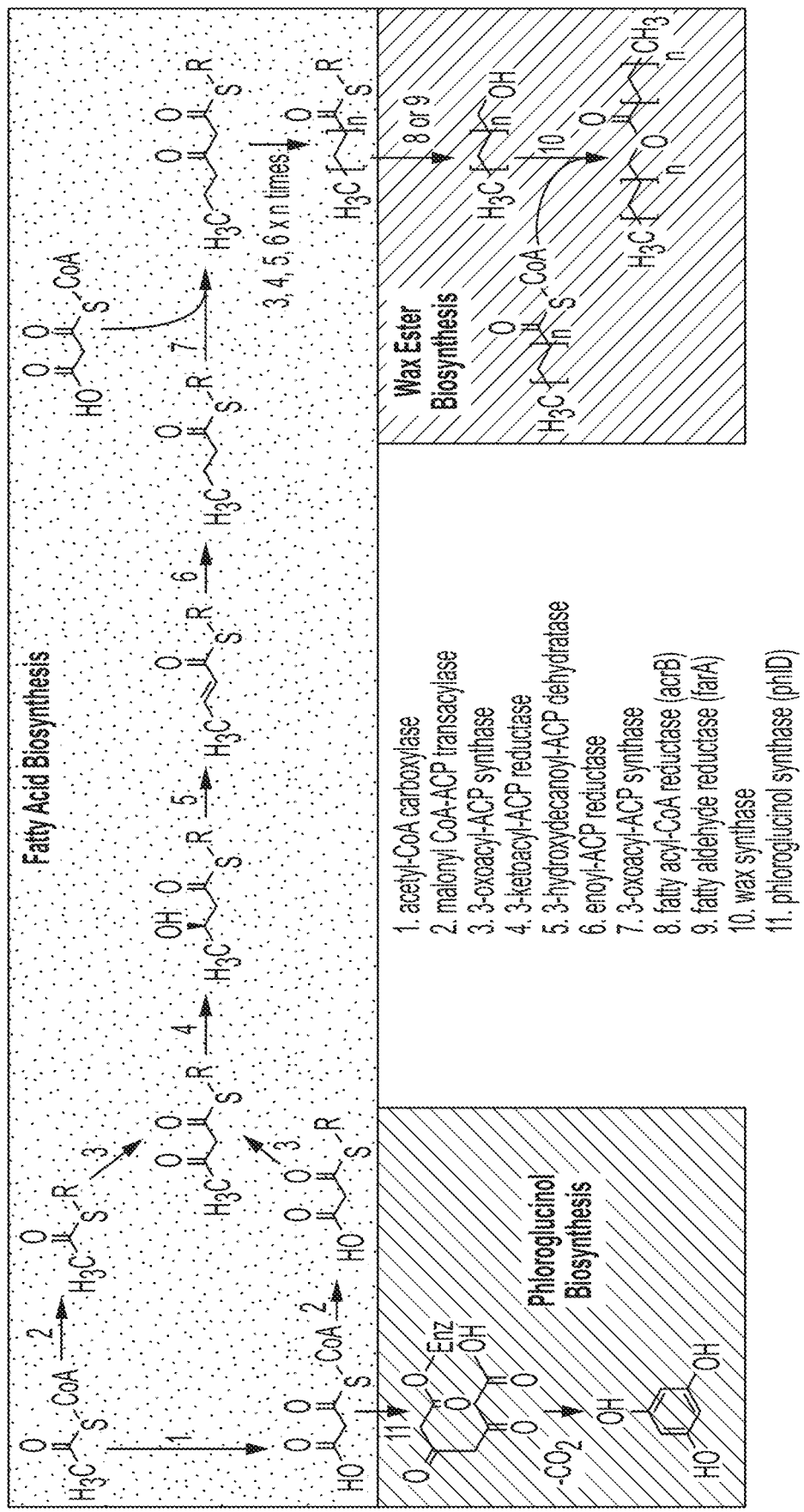
FIG. 8 is an illustration of and wax ester biosynthesis pathway and potential for diversion to alternative products.
Figure 9A:
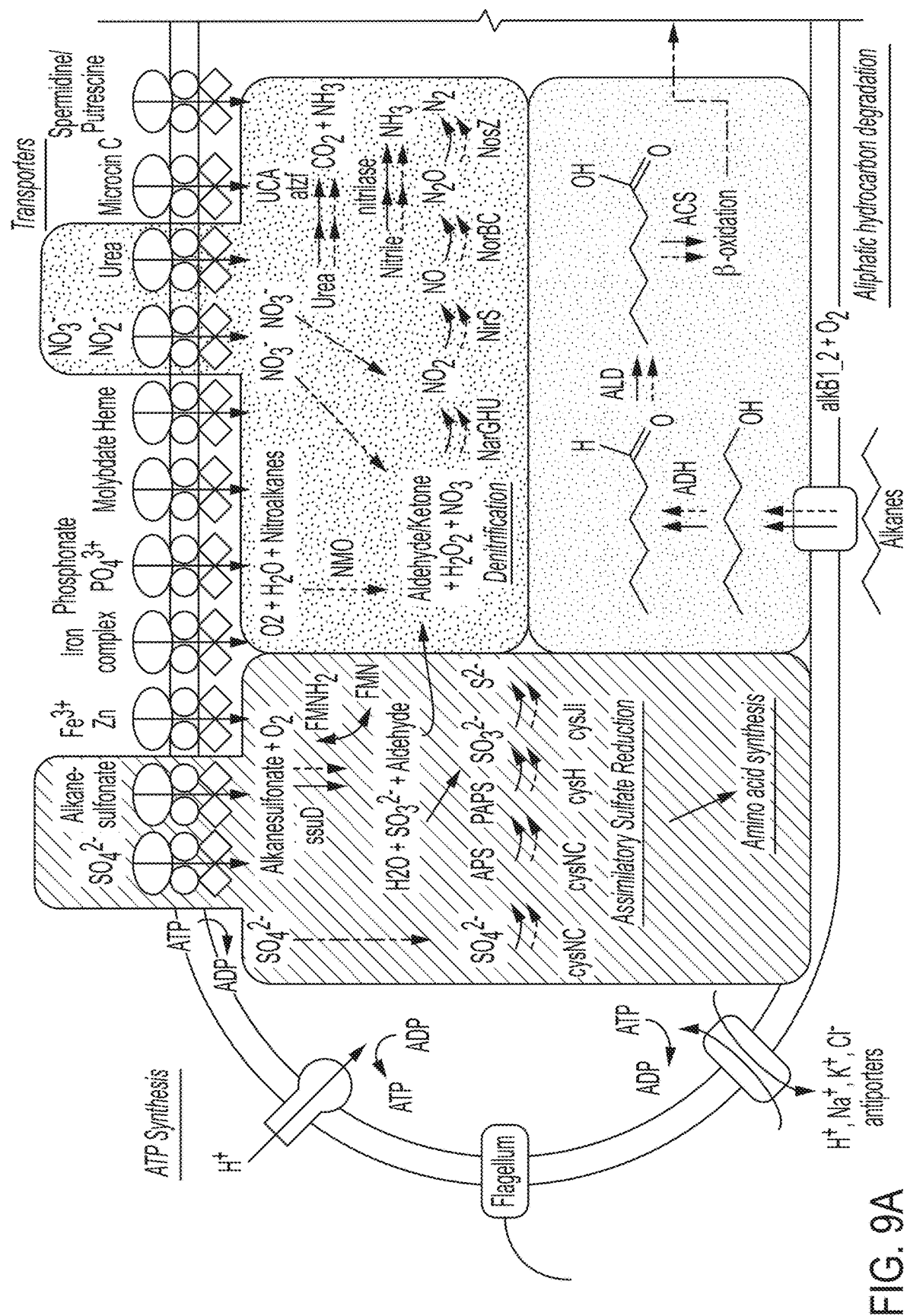
FIGS. 9A and 9B illustrate exemplary aromatic/alkane pathways (adapted from Evans et al., 2018).
Figure 9B:
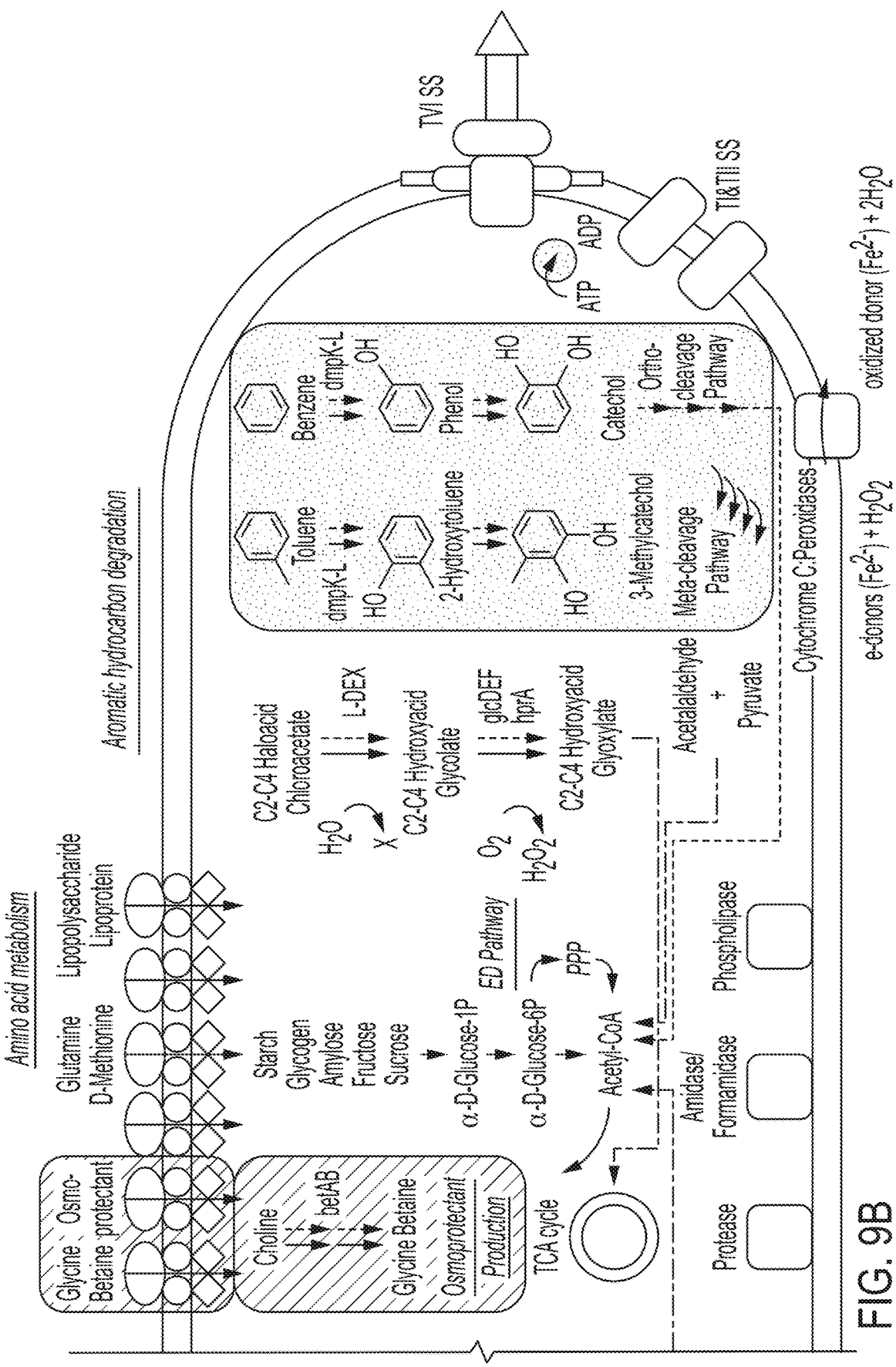
Figure 10:
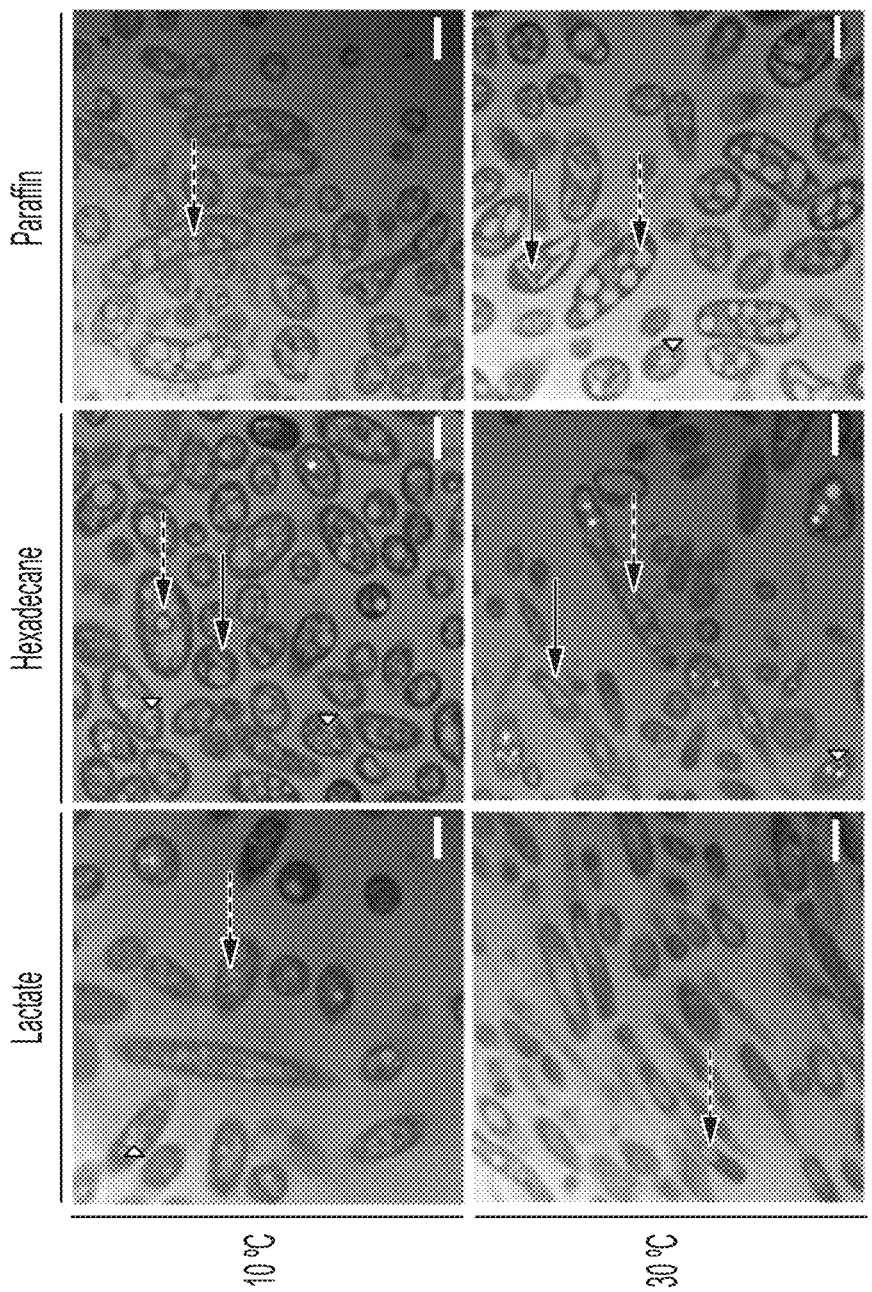
FIG. 10 is a transmission electron micrographs (adapted from Branchu et al., 2017) of planktonic and biofilm cells of *M. hydrocarbonclasticus* SP17 grown on lactate, hexadecane or paraffin. The bright inclusions are associated with lipid accumulation. The bars represent 1 µm.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of +10% of that stated.

As used herein, the term "oleaginous organism" refers to an organism with the ability to metabolize carbon substrates into lipids.

As used herein, the term "hydrocarbonoclastic organism" refers to an organism with the ability to metabolize aliphatic and/or aromatic hydrocarbons.

Overview

A bioreactor is configured to provide a high surface area solid scaffold suitable for the growth of oleaginous and/or hydrocarbonoclastic organisms such as *Marinobacter* spp., optimize mass transfer, and allow for continuous extraction of product between two liquid phases. This is expected to enable more efficient biotransformations, either of hydrophobic (e.g. petroleum) feedstocks into aqueous products or from aqueous feedstocks into hydrophobic products (e.g. lubricants).

The bioreactor may take a number of configurations as described herein, such as the packed-bed and extractive membrane types. For some embodiments of bioreactor design, many columns can be parallelized to scale production of a product while maintaining optimal mass transfer and fluid flow within the reactor. This modular design facilitates the removal and replacement of an individual column that become necessary (e.g., in cases of fouling), while minimizing the impact on the productivity of the overall bioreactor.

For example, a bioreactor system can include a combination of several or all of the following features: vessels for holding feedstock, supplemental nutrients, and extraction solution; pumps and flow controllers for controlling fluid introduction; fluidic channels to allow for the routing of solutions into the bioreactor; valves enabling control of individual fluid streams; a fluidic mixer; an aerator for the introduction of dissolved gases; a bubble trap for removal of gas bubbles; thermally-jacketed bioreactor chamber(s) used for product synthesis; a system for introducing acid or base to adjust pH; sensors for monitoring reaction conditions, including pH, dissolved gases, planktonic cell density, biofilm cell density, temperature, flow rate, conductivity, pressure, bioavailable nitrogen species, dissolved organic carbon, organic acids, genetic material, and/or minerals; connection to a system for chemical analysis of the output (such as HPLC, GC-MS, ICP, and the like); a phase separator for separating the solvent and aqueous phases; a module for product purification; a vessel for product storage; a fluidic path and associated pumps and valves to allow recirculation of the product extraction solution through the bioreactor; a fluidic path and associated pumps, valves, and reservoirs to allow recirculation of the feedstock solution through the bioreactor; and a computer control system operably connected to monitor sensors and actuate valves.

The biofilm-forming microorganism can be one or more of a number of different organisms. Preferably it is hydrocarbonoclastic and/or oleaginous. For example, naturally occurring *Marinobacter* sp. can be used to convert aromatics, alkanes, short chain fatty acids or other feedstocks into wax esters. In alternative embodiments, engineered *Marinobacter* sp. are used to redirect carbon flux from fatty acid ester production to the production of alternative products.

Suitable organisms for use in this technique can include, but are not limited to, *Aestuariibacter aggregatus* WH169, *Aestuariibacter* OTU3, *Acinetobacter baylyi* ADP1, *Acinetobacter* sp. H01-N, *Alcanivorax borkumensis* SK2, *Alcanivorax jadensis* T9, Alkanidiges, *Alteromonas* sp. strain TK-46, *Alteromonas macleodii*, *Alteromonas macleodii* NBRC 102226, *Alteromonas macleodii* 107, *Arcobacter* UTICA-S4D1, *Arcobacter* MARC-MIP3H16, *Bacillus subtilis*, *Colwellia*, *Cycloclasticus*, *Escherichia coli*, *Escherichia fergusonii*, *Escherichia fergusonii* ATCC 35469, *Halomonas*, *Halomonas* sp. strain TG39, *Marinobacter adhaerens*, *Marinobacter algicola*, *Marinobacter alkaliphilus*, *Marinobacter antarcticus*, *Marinobacter aquaeolei*, *Marinobacter aquaeolei* VT8, *Marinobacter atlanticus*, *Marinobacter gudaonesis*, *Marinobacter hydrocarbonoclasticus*, *Marinobacter hydrocarbonoclasticus* SP17, *Marinobacter maritimus*, *Marinobacter salsuginis*, *Marinobacter santoriniesis*, *Marinobacter squalenivorans*, *Marinobacter* sp. UTICA-S1B6, *Mortierella isabellina*, *Oceanospirillales*, *Oleispira*, *Pseudoalteromonas*, *Pseudoalteromonas* sp strain TG12, *Pseudomonas aeruginosa*, *Pseudomonas aeruginosa* LST-03, *Pseudomonas aeruginosa* PST-01, *Pseudomonas putida*, *Pseudomonas putida* IH-2000, *Pseudomonas putida* DOT-TIE, *Pseudomonas putida* S12, *Rhodococcus opacus* PD630, *Rhodocuccus ruber*, *Saccharomyces cerevisiae*, *Thalassospira* sp. TK-13, *Thalassospira xanhenis* P-4, *Thalassolituus*, *Yarrowia lipolytica*, and isolates from Bacosa et al., 2018. Additional organisms that are suitable for use in the bioreactor include *Streptomyces atlanticus*, *Streptomyces griseus*, *Streptomyces lividans*, *Streptomyces coelicolor*, *Labrenzia aggregata*, *Labrenzia alexandrii*, and members of the Biocathode MCL consortium from Wang, 2015. Further contemplated herein are combinations of any of the above organisms.

Systems to control the introduction and removal of fluids may be included. Suitable containers for liquids, fluidic channels (such as tubing, pipes, joints, and the like), valves, pumping systems, flow sensors, and computer control of fluid flow are contemplated. In various cases, a configuration employing gravity may eliminate the need for one or more pumps. Sensors monitoring biofilm health, system oxygenation, pH, and/or chemicals present in the feedstock or extraction solutions may also be included. The computer control system may dynamically respond to sensor readouts to alter flow rates, adjust nutrient or gas concentrations, or notify the operator about a system failure.

Further contemplated are methods of using the bioreactor for converting a petroleum product into an aqueous product, methods for converting an aqueous feedstock into a hydrophobic product, methods for converting a complex aqueous feedstock into a single aqueous product and methods for the production of lubricants.

Various embodiments can include an electrode operable as a terminal electron sink or source effective to facilitate enzymatic processes.

DETAILED DESCRIPTION OF THE PREFERRED EMBODIMENTS

Biofilms for Biosynthesis or Biotransformation

Biofilm-forming organisms form a layer on a surface, entrapping cells in a self-produced extracellular matrix. Biofilms can consist of either an individual type of organism or consist of a consortium of multiple different species/strains. Frequently, cells exhibit altered gene expression when growing in a biofilm, which can lead to more efficient utilization of nutrients or the enhanced production and/or accumulation of a particular biosynthetic product. In addition, biofilms can support a significantly higher biomass density than suspended cell culture, which can enable higher kinetics for biosynthesis and higher concentrations of a final product. In particular, biofilms are well suited for syntheses requiring multi-step enzymatic pathways (Muffler et al., 2014), as the system readily facilitates spatial compartmentalization of individual reaction steps, without the need to purify the product between each step. Organisms in biofilms display enhanced robustness, demonstrating greater durability as well as increased chemical resistance in comparison to planktonic cells. These attributes make biofilms an advantageous medium for biosynthesis or biotransformation.

Continuous Manufacturing

Because biofilms remain supported by a solid scaffold, they can facilitate continuous manufacture of a product in a stationary phase. Unlike in many cell suspension fermentation reactions, where significant resources go into the production of cell biomass along with product synthesis, in stationary phase synthesis, the total biomass remains practically constant throughout the course of product synthesis.

Oleaginous and Hydrocarbonclastic Organisms

Species from *Marinobacter, Thalassolituus, Oleispira, Acinetobacter, Alkanidiges* among others can metabolize alkanes and other hydrocarbon compounds. Many of these organisms can survive using hydrocarbons as their sole carbon source, with n-alkane oxidation producing acyl-CoA metabolites. Alkanes are first converted to alkanol by an alkane hydroxylase, which is then converted into an alkanal by an alcohol dehydrogenase. The alkanal is converted to Acyl-CoA by acyl-CoA synthase (Manila Perez, 2010). Excess carbon is often routed to the production of wax esters (Knutson, 2017), that can accumulate within the cell in inclusions or potentially be excreted by the cell (Manilla-Perez, 2010). Wax esters are produced enzymatically in the cells through the activation of fatty acids to either an acyl-CoA or acyl-ACP substrate. A portion of these substrates are then converted to a fatty alcohol. A fatty alcohol and fatty aldehyde-CoA (fatty-aldehyde-ACP) are combined to form a final wax ester product. The wax ester pathway can be rerouted to produce other compounds, as demonstrated through the production of phloroglucinol in Meyer et al., 2019. Often, these organisms form biofilms at the interface between a hydrophobic solution such as petroleum and an aqueous medium, and are able to survive with compounds from the hydrophobic solution as the sole carbon source for the organism. In the context of a biofilm, *Marinobacter* spp. and other organisms may exhibit increased productivity compared to suspended cell culture (Klein et al., 2007).

Type II secretion systems (T2SS) are important for biofilm formation and play a role in the mass transfer of alkanes into the cells (Ennouri et al., 2017). In some embodiments, upregulation of T2SS and associated proteins that support alkane uptake is used to enhance the rate of alkane metabolism. Additionally, the AupA and AupB membrane proteins play a role in alkane uptake into the cell (Mounier et al., 2018). Upregulating expression of these proteins can be used to increase the efficiency of alkane uptake.

In some hydrocarbonoclastic organisms, lipids can be exported from the cells, which can be used to facilitate better product extraction (Manilla-Perez et al., 2010; Nakano et al., 2012). In some embodiments, organisms producing biosurfactants such as glycolipids may be used to increase product extraction.

Certain species of the *Marinobacter, Oleispira, Alcanivorax*, and *Halomonas* genera, among others, are halotolerant (can be classified as slight to extreme halophiles), growing in salinities ranging from 1.7-30%. The use of these organisms can facilitate biosynthesis in seawater or even more extreme saline conditions.

One advantage of *Marinobacter*, in particular, is that experimental data indicates that *Marinobacter atlanticus* can produce stable biofilms that can be as little as 10 μm thick. A thin, stable biofilm is advantageous in a biofilm bioreactor because it improves mass transport and reduces the risk of fouling/clogging in the bioreactor. To optimize transport of reagents and products in and out of the biofilm, the total thickness should be less than 150 μm.

Controlling Biofilm Dispersal

Natural biofilms undergo cycles of growth and dispersal that is driven by environmental cues. To facilitate efficient continuous synthesis, it is desirable to control the planktonic nature of the cells and inhibit dispersal during synthesis. Bis-(3'-5')-cyclic dimeric guanosine monophosphate (c-di-GMP) is a signaling molecule responsible for regulating cell surface traits, secretion, cell adhesion, motility, and biofilm formation (Hengge, 2009). c-di-GMP is synthesized from guanosine triphosphate by diguanylate cyclase enzymes and is broken down by phosphodiesterase enzymes. Diguanylate cyclase enzymes contain a GGDEF (SEQ ID NO: 1) domain that is responsible for c-di-GMP synthesis while phosphodiesterases contain an EAL domain responsible for c-di-GMP degradation. It has been demonstrated that an overproduction of GGDEF (SEQ ID NO: 1) domain proteins increases the synthesis of molecules required for biofilm formation, such as adhesins and matrix components, while interfering with motility functions. In a corollary manner, overproduction of EAL domain proteins led to the opposite behavior. In one embodiment of the invention, the biofilm forming organism will be engineered to control the expression of GGDEF (SEQ ID NO: 1) and EAL domain proteins. Through the use of an inducible promoter, microorganisms can be grown in planktonic phase to establish an initial culture by inducing EAL domain proteins and repressing GGDEF (SEQ ID NO: 1) domain proteins, and then minimally disperse upon biofilm formation, through expression of GGDEF (SEQ ID NO: 1) domain proteins and suppression of EAL domain proteins (Hengge, 2009). In an alternative embodiment expression of CsrA, a carbon storage regulator, can be regulated to control biofilm formation. Suitable activators of inducible promoters can be provided, for example, when introducing feedstock and/or nutrients.

Packed Bed Bioreactor

For one embodiment of the invention, product synthesis takes place in a packed bed bioreactor. Packed bed reactors, also known as fixed bed bioreactors, contain granular solid supports for biofilm growth. These particles are densely packed within the bioreactor to maximize surface area to volume ratio. The particle diameter can range between 5 μm to 20 mm. The size of the particles determines the pore size and can be used to control percolation of the feedstock through the packed bed reactor. In some embodiments, particles of multiple sizes may be used to control packing density and biofilm formation. In further embodiments, the particle diameter will be in the range of 5-100 μm. Small particle diameters with thin biofilms can maximize total biomass in the reactor, while minimizing the potential for clogging.

The vessel containing the carrier beads is in a columnar geometry, with a fluid inlet on one end and outlet on the opposite end. The diameter of the column can be proportional to the particle diameter, ranging from 5-1000×the particle diameter. In certain embodiments, the column diameter may be more than 1000×the particle diameter; in these configurations, specialized fittings may be used to impedance match flow from the input source to flow in the column. In particular, a distributor plate may be used at the column inlet to evenly distribute flow across the column cross-section. The length of the column is selected by the time in contact with the biofilm required to process the majority of the feedstock. In some implementations, a shorter column can be used, with the feedstock recycled through the column. The column can be made of any suitable materials such as polyvinylchloride, glass, etc.

Product Recovery from a Packed Bed

To overcome product extraction limitations experienced in packed reactors, a solvent phase is periodically or continuously circulated through the reactor to extract a hydrophobic product that is soluble in the solvent phase. In some embodiments, a droplet of a liquid phase that is immiscible with water forms a plug that completely excludes the aqueous phase as it is introduced into the bioreactor. The aqueous phase solution is introduced following the plug and the water pressure pushes the plug through the system. A valve at the inlet allows the switching between the two liquid phases. The time for which the cells are exposed to solvent in the reactor must balance the required extraction time and cell toxicity, with the duration of exposure is set by the flow rate, and the height/volume of the immiscible plug. The immiscible phase can be recirculated through the reactor to fully extract the desired product. In another embodiment, the solvent phase is dispersed into small droplets that are introduced into the reactor as a suspension in water, such that at the outlet of the reactor, the solvent phase droplets can be coalesced and separated from the aqueous phase.

At the outlet of the bioreactor, a separator is used to divide the aqueous and organic streams. In some embodiments, a hydrophobic membrane is used to exclude the aqueous phase while allowing the hydrophobic phase through. In another embodiment, active valving is used to route the hydrophobic phase into a separate channel. In yet another embodiment, the mixed solution is routed into a chamber where gravity separation is used to segregate the two liquid phases.

Magnetic Carrier Beads

In one embodiment, the carrier beads can be made from a ferromagnetic material. To extract product from the biofilm immobilized on the carrier beads, a magnetic field can be applied to move the carrier beads from the aqueous feedstock phase into a solvent phase for product extraction.

Packed Bed Bioreactor Scaffold Materials

A variety of different scaffold materials may be used to support biofilm growth. In some cases, these scaffolds may be particles with a generally spherical shape. In other cases, the scaffolds may be small ring-shaped structures. Suitable materials include, but are not limited to polymers, carbonized agricultural byproducts, expanded clay, silica, alumina, iron oxide, metal, graphite, or carbon nanostructures. In some embodiments the support material is conductive, allowing for electron transfer to or from the biofilm.

The potential degradation of the scaffold material, either by the organism itself or by components of the feedstock or extraction solutions should to be considered as a selection criteria. In some cases, the particles may be metabolized by the biofilm either serving as the primary feedstock or providing supplemental nutrition for the biofilm. In other cases, the support material may be resistant to temperature and/or chemical treatments that allow for elimination of the biofilm followed by repopulation with a new biofilm, either to change the product produced in the reactor or to restore reactor productivity.

Membrane Bioreactor

In an embodiment of the invention, a bioreactor with a membrane that supports a biofilm between two liquid phases is used for the biosynthesis and extraction of a product. One type of membrane bioreactor, the extractive membrane bioreactor, is currently used for the treatment of wastewater. The extractive membrane bioreactor consists of a membrane between two aqueous liquids, a wastewater zone that may contain a high level of organic compounds and a biological zone, where the waste materials are metabolized/degraded. A membrane between the two zones both supports a biofilm and facilitates the selective transport of organics into the biological zone.

Product Recovery from a Membrane Bioreactor

In one embodiment, solvent is introduced onto one side of the membrane and an aqueous feedstock onto the other side of the membrane. A hydrophobic product is produced in the biofilm on the aqueous side of the membrane, and a solvent continuously flows on the opposite side of the membrane extracting the product from the biofilm. The solvent can be recirculated in the system to concentrate the extracted product. In an alternative embodiment, a hydrophobic feedstock is introduced on one side of the membrane and a hydrophilic product is produced by the biofilm on the opposite side of the membrane and extracted into an aqueous phase. In yet a further embodiment, an aqueous feedstock is introduced on the biofilm-containing side of a chemically-selective membrane and the purified product is extracted on the opposite side of the membrane.

In some embodiments, the membrane is formed into a tubular structure, where one liquid phase is on the outside of the tube and the other liquid phase is inside the tube. Liquid from two different sources is introduced into the tube through a concentric manifold. A valve upstream of the manifold allows an aqueous medium to be routed to both sides of the membrane, which could be used to help promote growth of the biofilm, rinse the system, or for other purposes.

Membrane Structure and Materials

In some embodiments, the membrane is a highly porous scaffold that is fully intercalated by the biofilm, which creates a barrier layer between the two liquid phases. This highly porous scaffold can be a polymer, graphene, porous glass or metal. In some implementations, the scaffold material is a cryogel, a macroporous structure created by rapidly freezing in a cryobath, followed by thawing (Berillo et al., 2019). In an alternative embodiment, the membrane is chemically selective. These membranes may be made from polymers, ceramics, or graphene oxide. The membrane material is selected based on the target chemical and can either function through size exclusion, electrostatic repulsion, or other hydrophobic/hydrophilic interactions.

Bioreactor System

In the bioreactor system, a bioreactor chamber contains a biofilm that is used to synthesize and extract a desired product. In addition to the bioreactor chamber, the bioreactor system typically includes reservoirs, pumps, valves, flow controllers, sensors, and a computer control system. Solutions are routed among these components using fluidic channels. Some embodiments of the invention may also include mixers, systems for introducing gas, output analysis, a phase separator, and a product purification module.

A pumping system may be used to propel fluid through the bioreactor system. Separate pumps may be used for each liquid stream or valving may be used to allow a single pump to be used for multiple streams. In one embodiment, pumps that do not require direct contact with the fluid, such as peristaltic or pressure-driven pumps, are used. Non-contact pumping is advantageous, as the system will be less impacted by potential biofouling and clogging. In various cases, a configuration employing gravity may eliminate the need for one or more pumps.

Some embodiments of the invention will have additional inlets for the introduction of gases. In some cases, gases may be used as a feedstock (e.g., ethylene, methane, carbon dioxide) and/or required for respiration (oxygen).

To prevent gas arising from bacterial respiration from causing blockages in the reactor, some embodiments will employ bubble traps, a type of fluidic structure using a porous polytetrafluoroethylene membrane, to eliminate gas from the reactor. In other embodiments, organisms that can fix carbon dioxide will be introduced into the biofilm community to facilitate gas removal and will thereby lower the overall carbon emissions of the reactor system. Organisms such as *Candidatus* Tenderia electrophaga are known to fix carbon dioxide and naturally live in biofilm consortia with organisms such as *Marinobacter* (Eddie et al., 2016). To facilitate efficient carbon fixation, some embodiments use a conductive biofilm scaffold with an applied potential. The control of surfactant production by the biofilm or the introduction of additional surfactants into the bioreactor, provides yet another means of gas bubble removal, as the use of soluble surfactants has been shown to promote gas bubble dissolution (Hanwright et al., 2005).

In some embodiments, multiple biofilm-containing vessels are connected in parallel, and a fluidic manifold is used to distribute the solution to the individual vessels. Parallelizing the vessels in this way can allow the scaling of production without altering the shear forces and mass transport within the overall reactor, thus mitigates some of the challenges traditionally associated with scalability of biofilm reactors.

Some embodiments include a thermal jacket to heat or cool the reactor. The thermal jacket may surround the reactor as a whole or the individual vessels. The thermal jacket is used to maintain the optimal temperature for synthesis. A temperature sensor (such as a thermocouple, resistive temperature detector, and the like) can monitor temperature which can be regulated under closed-loop control.

One or many sensors may be used to monitor and regulate fluid flow and reaction conditions. Sensors may include, but are not limited to: pH, temperature, oxygen (and other dissolved gases), optical signatures (absorbance, Raman, fluorescence) of chemical components, cell density (either in the biofilm or planktonic), pressure, and flow rate. Pressure and flow rate sensors can provide information about reactor clogging and/or conditions where shear forces may cause biofilm disruption. In embodiments where the bioreactor contains multiple vessels in parallel, sensors can monitor both system performance as a whole, or the performance of individual vessels.

A computer (such as a single board computer) or other digital control system is used to control pumps, valves, the thermal system, and monitor the sensors. The computer processes the sensor inputs and sends signals to the thermal jacket to adjust the temperature, can open and close valves or adjust the rate of pumping to control the introduction of feedstock and/or extraction solutions, and can alert the operator to performance degradation, contamination, or clogging.

In one embodiment, three reservoirs, for the feedstock solution, supplemental nutrients, and for the extraction solution, are connected to the inlet of a thermally jacketed bioreactor via a series of fluidic channels. A fluidic channel at the outlet of each reservoir may have an individual pump and flow controller (FC). These fluidic channels are routed to a series of multi-way valves that merge the three fluidic channels and allow for controlled routing of an individual or mixture of the source solutions into a single channel that enters the bioreactor.

In an alternative embodiment, such as for a membrane bioreactor, two or more fluidic channels enter the bioreactor, with a series of channels and valves allowing any mixture of the three source solutions to be introduced into each inlet of the bioreactor. To fully mix or emulsify solutions before entering the bioreactor a mixer may be included in-line ahead of the bioreactor inlet. Some embodiments may contain an aerator ahead of the bioreactor inlet to facilitate the introduction of oxygen as needed for respiration, or other gases that may serve as feedstocks. To enable adjustment of pH in the bioreactor, acid and base reservoirs may be connected to the bioreactor with a pump and a multiway valve allowing controlled introduction of either acid or base.

The outlets of the reactor can be routed for recirculation, purified and to a product reservoir, and/or to a waste stream. A series of fluidic channels and valves controls the route of the outlet solutions in response to process conditions. Immediately following the outlet, a phase separator may be used to route immiscible solutions to separate process paths. Downstream of the bioreactor outlet and phase separator, there may be a module for product purification and extraction. The outlet of this module can be routed to a product storage tank.

In some embodiments, the spent feedstock can be recirculated with the addition of additional feedstock molecules, nutrients, or other components introduced as required. Additionally, the product-containing solution can be recirculated to extract more product and increase the total product concentration in the solution. Valves control the routing of the output solutions, enabling control over recirculation. Storage reservoirs may be included in the recirculation fluidic route(s) along with pumps and valves to enable controlled introduction of recirculated solutions in response to process conditions. A valve can be connected so as to allow either recirculating flow or flow to further downstream processing.

A sensor module may be included at the outlet of the bioreactor to monitor process conditions. Each reservoir and system module may also contain additional sensors to monitor quality and allow adjustment of process conditions. In some embodiments a valved fluidic path may allow for fluid sampling of the output of the bioreactor, phase separator, and/or purification module for chemical analysis. The fluid may be routed to a GC-MS, LC-MS, ICP or other analytical instruments for this analysis.

Multi-Step Enzymatic Processes

To facilitate multi-step enzymatic processes, in some embodiments, the bioreactor system contains multiple biofilm reactor modules, wherein each module carries out a separate enzymatic step required to make a desired product. The bioreactor system contains fluidic channels to route an intermediate or product between each module. Some embodiments may utilize the membrane bioreactor and packed bed bioreactor in individual modules. For example, a product extracted with a solvent droplet in the packed bed reactor can be routed into a membrane bioreactor for a subsequent process step. In some embodiments, purification or separation modules are utilized between biofilm reactor modules.

Biofilm Lyophilization

Biofilms can be tolerant to desiccation, allowing a biofilm to be fully dehydrated and still remain viable upon rehydration. To enable production of a particular product on demand, a biofilm comprising one or more organisms can be established on a solid support (such as a membrane or carrier beads) and dried for storage through a technique such as lyophilization. In some embodiments, the carrier beads will be packed in a bioreactor column, the biofilm established and then desiccated, while in other embodiments, the biofilm will be established on carrier beads, the biofilm will be desiccated, and prior to synthesis the beads will be packed in a bioreactor column and rehydrated.

EXAMPLES

Example 1: Conversion of Hydrophobic Feedstock into Aqueous Phase Product

Hydrophobic feedstocks refer to liquid solutions that are immiscible with water. Examples of hydrophobic feedstocks include crude oil, refined petroleum, and solvent waste. Typically these feedstocks consist of non-polar organic chemicals such as aromatic or aliphatic compounds. The compounds in the feedstock can be metabolized by organisms in the biofilm or otherwise biotransformed either by the organisms themselves or enzymes in the biofilm extracellular matrix.

To produce a water-soluble product such as acetate or caprolactone, from a hydrophobic feedstock:
  *Marinobacter* is engineered to produce a water-soluble product of interest
  *Marinobacter* is grown in planktonic culture to an OD of 0.1-2
  The planktonic culture is circulated through the bioreactor to seed either the membrane or the support particles.
  The bioreactor circulates nutritive media until the biofilm is fully formed, 1-400 hours.
  The feedstock is continuously introduced into the bioreactor along with an aqueous solution into which the product is extracted. The aqueous solution also contains fixed nitrogen species (ammonium, nitrate, nitrite), sodium ions, and trace minerals to support the biofilm.
    In the packed bed bioreactor, the feedstock is introduced as an emulsion with the aqueous phase. Droplets of the feedstock will be trapped in the biofilm and metabolized/converted into an aqueous soluble product that is then excreted by the organisms and collected in the aqueous phase.
    In the membrane bioreactor, the hydrophobic feedstock flows on one side of the membrane and the aqueous solution flows on the other. The hydrophobic feedstock diffuses through the membrane and into the biofilm and is metabolized/converted into a product that is excreted by the organisms and collected in the aqueous phase on the opposite side of the membrane.
  The aqueous phase can be recirculated back through the reactor, as needed to concentrate the product.
  The product is collected and purified from the aqueous solution. The purification step can include desalting and evaporation.

Example 2: Conversion of Aqueous Feedstock into Hydrophobic Product Such as Wax Esters To produce wax esters from an aqueous feedstock:
  *Marinobacter* was grown in planktonic culture to an OD of 0.1-2
  The planktonic culture was circulated through the bioreactor to seed either the membrane or the support particles.
  The bioreactor circulated nutritive media until the biofilm was fully formed, 1-400 hours
  In a packed bed reactor, the feedstock was circulated through the bioreactor for 1-24 hours, then when optimal product formation is achieved, a valve was actuated introducing a solvent bolus into the bioreactor to extract product.
  In a membrane reactor, the feedstock can be circulated on the exterior of a tubular membrane and a solvent is circulated through the core of the tubular membrane.
  The wax esters are miscible with the solvent phase and so can be extracted into the solvent.
  The solvent phase can be recycled until it is saturated with product
  The product was extracted from the solvent and purified.

Example 3: Conversion of Mixed Aqueous Feedstock into Aqueous Product

To produce acetate from a feedstock of mixed organic waste:
  A biofilm forming organism is grown in planktonic culture to an OD of 0.1-2
  The planktonic culture is circulated through the bioreactor to seed either the membrane or the support particles
  The bioreactor circulates nutritive media until the biofilm is fully formed, 1-400 hours in a packed bed reactor, the feedstock is circulated through the bioreactor. The packed bed is contained by a chemically selective membrane that allows the product to pass through into a collection stream.
  In a membrane reactor, the biofilm is grown on the inside of a chemically selective membrane. As the product is synthesized, it passes through the membrane and is extracted.
  Pressure across the membrane can concentrate the product in the collection stream.
  The product is collected and water is removed.

CONCLUDING REMARKS

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Arroyo, J. L. N., Cifuentes, S. F., Hernendez, A. d. A. R., Parada, J. S.; 2013. Biological method for the degradation of complex mixtures of hydrocarbons in an aqueous phase, ES Patent Application 2491965B1

Berillo, D. A., Caplin, J. L., Cundy, A. B. and Savina, I. N., 2019. A cryogel-based bioreactor for water treatment applications. Water research, 153, pp. 324-334.

Bacosa, H. P., Kamalanathan, M., Chiu, M. H., Tsai, S. M., Sun, L., Labonte, J. M., Schwehr, K. A., Hala, D., Santschi, P. H., Chin, W. C. and Quigg, A., 2018. Extracellular polymeric substances (EPS) producing and oil degrading bacteria isolated from the northern Gulf of Mexico. PloS one, 13(12).

Daugulis, A. J., Collins, L. D., 1997. Two-phase partitioning bioreactor for the degradation of a xenobiotech, Ca. Patent Application 2216327C.

Eddie, B. J., Wang, Z., Malanoski, A. P., Hall, R. J., Oh, S. D., Heiner, C., Lin, B. and Strycharz-Glaven, S. M., 2016.

'Candidatus Tenderia electrophaga', an uncultivated electroautotroph from a biocathode enrichment. International journal of systematic and evolutionary microbiology, 66(6), pp. 2178-2185.

Ennouri, H., d'Abzac, P., Hakil, F., Branchu, P., Naïtali, M., Lomenech, A. M., Oueslati, R., Desbrières, J., Sivadon, P. and Grimaud, R., 2017. The extracellular matrix of the oleolytic biofilms of *Marinobacter hydrocarbonoclasticus* comprises cytoplasmic proteins and T2SS effectors that promote growth on hydrocarbons and lipids. Environmental microbiology, 19(1), pp. 159-173.

Evans, M. V., Panescu, J., Hanson, A. J., Welch, S. A., Sheets, J. M., Nastasi, N., Daly, R. A., Cole, D. R., Darrah, T. H., Wilkins, M. J. and Wrighton, K. C., 2018. Members of *Marinobacter* and *Arcobacter* influence system biogeochemistry during early production of hydraulically fractured natural gas wells in the appalachian basin. Frontiers in microbiology, 9, p. 2646.

Gauthier, M. J., Lafay, B., Christen, R., Fernandez, L., Acquaviva, M., Bonin, P. and Bertrand, J. C., 1992. *Marinobacter hydrocarbonoclasticus* gen. nov., sp. nov., a new, extremely halotolerant, hydrocarbon-degrading marine bacterium. International Journal of Systematic and Evolutionary Microbiology, 42(4), pp. 568-576.

Hanwright, J., Zhou, J., Evans, G. M. and Galvin, K. P., 2005. Influence of surfactant on gas bubble stability. Langmuir, 21(11), pp. 4912-4920.

Hengge, R., 2009. Principles of c-di-GMP signalling in bacteria. Nature Reviews Microbiology, 7(4), pp. 263-273.

Hejazi, M. A., Holwerda, E. and Wijffels, R. H., 2004. Milking microalga *Dunaliella salina* for β-carotene production in two-phase bioreactors. Biotechnology and bioengineering, 85(5), pp. 475-481.

Hejazi, M., Wijffels, R., Holwerds, E. and Tramper, J., Cognis Deutschland GmbH and Co KG, 2005. Process for obtaining carotenoids from natural sources. U.S. patent application Ser. No. 10/513,816.

Holladay, D. W., Hancher, C. W., Scott, C. D. and Chilcote, D. D., 1978. Biodegradation of phenolic waste liquors in stirred-tank, packed-bed, and fluidized-bed bioreactors. Journal (Water Pollution Control Federation), pp. 2573-2589.

Jackson, B. A., Bahri, P. A. and Moheimani, N. R., 2017. Repetitive non-destructive milking of hydrocarbons from *Botryococcus braunii*. Renewable and Sustainable Energy Reviews, 79, pp. 1229-1240.

Klein, Benjamin, Vincent Grossi, Patrick Bouriat, Philippe Goulas, and Régis Grimaud. "Cytoplasmic wax ester accumulation during biofilm-driven substrate assimilation at the alkane-water interface by *Marinobacter hydrocarbonoclasticus* SP17." Research in microbiology 159, no. 2 (2008): 137-144.

Klein, B., Grossi, V., Bouriat, P., Goulas, P. and Grimaud, R., 2008. Cytoplasmic wax ester accumulation during biofilm-driven substrate assimilation at the alkane-water interface by *Marinobacter hydrocarbonoclasticus* SP17. Research in microbiology, 159(2), pp. 137-144.

Knutson, C. M., Lenneman, E. M. and Barney, B. M., 2017. *Marinobacter* as a model organism for wax ester accumulation in bacteria. Biogenesis of fatty acids, lipids and membranes. Springer International Publishing, Cham, pp. 1-22.

Lattuati, A., Metzger, P., Acquaviva, M., Bertrand, J. C. and Largeau, C., 2002. n-Alkane degradation by *Marinobacter hydrocarbonoclasticus* strain SP 17: long chain β-hydroxy acids as indicators of bacterial activity. Organic Geochemistry, 33(1), pp. 37-45.

Livington, A., Evonik Membrane Extraction Technology Ltd., 1998. Membrane separation involving a two-phase fluid. G.B. Patent Application 2338910A.

Manilla-Pérez, E., Lange, A. B., Hetzler, S. and Steinbüchel, A., 2010. Occurrence, production, and export of lipophilic compounds by hydrocarbonoclastic marine bacteria and their potential use to produce bulk chemicals from hydrocarbons. Applied microbiology and biotechnology, 86(6), pp. 1693-1706.

Meyer, A., Saaem, I., Silverman, A., Varaljay, V. A., Mickol, R., Blum, S., Tobias, A. V., Schwalm III, N. D., Mojadedi, W., Onderko, E. and Bristol, C., 2019. Organism Engineering for the Bioproduction of the Triaminotrinitrobenzene (TATB) Precursor Phloroglucinol (PG). ACS synthetic biology, 8(12), pp. 2746-2755.

Mounier, J., Hakil, F., Branchu, P., Naïtali, M., Goulas, P., Sivadon, P. and Grimaud, R., 2018. AupA and AupB Are Outer and Inner Membrane Proteins Involved in Alkane Uptake in *Marinobacter hydrocarbonoclasticus* SP17. mBio, 9(3), pp. e00520-18.

Muffler, K., Lakatos, M., Schlegel, C., Strieth, D., Kuhne, S. and Ulber, R., 2014. Application of biofilm bioreactors in white biotechnology. In Productive Biofilms (pp. 123-161). Springer, Cham.

Nakano, M., Iehata, S., Tanaka, R. and Maeda, H., 2012. Extracellular neutral lipids produced by the marine bacteria *Marinobacter* sp. Biocontrol science, 17(2), pp. 69-75.

Sayre, R. T., Ohio State University Research Foundation, 2009. Optimization of biofuel production. U.S. patent application Ser. No. 12/328,695.

Wang Z, Leary D H, Malanoski A P, Li R W, Hervey W Jt, Eddie B J, Tender G S, Yanosky S G, Vora G J, Tender L M, Lin B, Strycharz-Glaven S M. 2015. A previously uncharacterized, nonphotosynthetic member of the Chromatiaceae is the primary CO2-fixing constituent in a selfregenerating biocathode. Appl Environ Microbiol 81:699-712

What is claimed is:

1. A bioreactor system comprising:
a column comprising a substrate coated with a biofilm comprising hydrocarbonoclastic and/or oleaginous organisms;
a first reservoir operably connected to deliver to the column a first liquid comprising a feedstock;
a second reservoir operably connected to deliver a second liquid to the column; and
a phase separator operably connected to receive both liquids from the column,
wherein the biofilm has a thickness of no greater than 150 µm and is effective to convert the feedstock into a desired product, and
wherein the phase separator is effective to separate the product from one or both of the liquids.

2. The bioreactor system of claim 1, further comprising:
a mixer operable either (1) to introduce either a dispersion of the two liquids into the column, or (2) to introduce a plug of the second liquid into a flow of the first liquid.

3. The bioreactor system of claim 1, wherein the column is a packed bed.

4. The bioreactor system of claim 1, wherein the substrate is a membrane effective to separate the two liquids.

5. The bioreactor system of claim 4, wherein the membrane is chemically selective.

6. The bioreactor system of claim 1, wherein substrate is conductive and facilitates electron transfer into and out of the biofilm.

7. The bioreactor system of claim 1, further comprising a plurality of columns connected in parallel.

8. The bioreactor system of claim 1, wherein the substrate operates as an additional feedstock for the biofilm.

9. The bioreactor system of claim 1, further comprising a pump and a valve configured to either recirculate liquids through the column or to direct liquids to the phase separator.

10. The bioreactor system of claim 9, further comprising:
a mixer operable either (1) to introduce either a dispersion of the two liquids into the column, or (2) to introduce a plug of the second liquid into a flow of the first liquid;
a thermal jacket effective to regulate temperature inside the column;
one or more sensors for monitoring reaction conditions; and
a computer control system operably connected to the one or more sensors, the pump, and the valve.

11. The bioreactor system of claim 1, wherein said organisms comprise *Marinobacter*.

12. A bioreactor system comprising:
a column comprising a substrate coated with a biofilm comprising hydrocarbonoclastic and/or oleaginous organisms;
a first reservoir operably connected to deliver to the column a first liquid comprising a feedstock;
a second reservoir operably connected to deliver a second liquid to the column; and
a phase separator operably connected to receive both liquids from the column,
wherein the biofilm has a thickness of no greater than 150 µm and is effective to convert the feedstock into a desired product,
wherein the phase separator is effective to separate the product from one or both of the liquids; and
wherein the bioreactor is configured as a packed bed bioreactor with particles having a diameter between 5 µm and 200 µm.

13. The bioreactor system of claim 12, wherein said organisms comprise *Marinobacter*.

14. A bioreactor system comprising:
a column comprising a substrate coated with a biofilm comprising hydrocarbonoclastic and/or oleaginous organisms;
a first reservoir operably connected to deliver to the column a first liquid comprising a feedstock;
a second reservoir operably connected to deliver a second liquid to the column; and
a phase separator operably connected to receive both liquids from the column,
wherein the biofilm has a thickness of no greater than 150 µm and is effective to convert the feedstock into a desired product,
wherein the phase separator is effective to separate the product from one or both of the liquids; and
wherein the bioreactor is configured as a packed bed bioreactor with particles having a diameter between 5 µm and 100 µm.

15. The bioreactor system of claim 14, wherein said organisms comprise *Marinobacter*.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1
```

```
Gly Gly Asp Glu Phe
1           5
```